United States Patent [19]
Carolan et al.

[11] Patent Number: 5,534,471
[45] Date of Patent: * Jul. 9, 1996

[54] ION TRANSPORT MEMBRANES WITH CATALYZED MIXED CONDUCTING POROUS LAYER

[75] Inventors: Michael F. Carolan; Paul N. Dyer, both of Allentown, Pa.

[*] Notice: The term of this patent shall not extend beyond the expiration date of Pat. No. 5,240,480.

[73] Assignee: Air Products and Chemicals, Inc., Allentown, Pa.

[21] Appl. No.: 180,938

[22] Filed: Jan. 12, 1994

[51] Int. Cl.$^6$ .............................. B01J 20/28; B01J 35/00
[52] U.S. Cl. .................. 502/4; 55/524; 95/54; 96/4; 502/324; 502/340
[58] Field of Search .............. 502/4, 324, 340; 55/524; 95/54; 96/4

[56] References Cited

U.S. PATENT DOCUMENTS

| | | | |
|---|---|---|---|
| 5,108,465 | 4/1992 | Bauer et al. | 55/16 |
| 5,160,618 | 11/1992 | Burggraaf et al. | 210/490 |
| 5,240,480 | 8/1993 | Thorogood et al. | 505/701 X |

Primary Examiner—Michael Lusignan
Attorney, Agent, or Firm—Keith D. Gourley

[57] ABSTRACT

The present invention relates to surface catalyzed ion transport membranes which demonstrate superior oxygen flux. The membranes comprise a porous mixed conducting multicomponent metallic oxide layer having a first surface onto which a catalyst is deposited and a second surface which is contiguous with a dense mixed conducting multicomponent metallic oxide layer. Suitable catalysts to be deposited onto the porous mixed conducting layer include one or more metals or oxides of metals selected from Groups II, V, VI, VII, VIII, IX, X, XI, XV and the F Block lanthanides of the Periodic Table of the Elements. The claimed membranes are capable of separating oxygen from oxygen-containing gaseous mixtures.

40 Claims, 1 Drawing Sheet

ION TRANSPORT MEMBRANES WITH CATALYZED MIXED CONDUCTING POROUS LAYER

TECHNICAL FIELD OF THE INVENTION

The present invention relates to ion transport membranes which are capable of separating oxygen from oxygen-containing gaseous mixtures. The membranes comprise a porous mixed conducting multicomponent metallic oxide layer having a first surface onto which a catalyst has been deposited and a second surface which is contiguous with a dense mixed conducting multicomponent metallic oxide layer.

BACKGROUND OF THE INVENTION

Solid state membranes formed from oxygen ionically conductive materials are showing promise for use in commercial processes for separating oxygen from oxygen-containing streams. Envisioned applications range from small scale oxygen pumps for medical use to large scale integrated gasification combined cycle (IGCC) plants. This technology encompasses two distinctly different membrane materials, solid electrolytes and mixed conductors. Membranes formed from mixed conductors are sometimes preferred over solid electrolytes in medium- and large-scale processes for separating oxygen from oxygen-containing gaseous mixtures because mixed conductors conduct both oxygen ions and electrons at elevated temperatures and can be operated without external circuitry such as electrodes, interconnects and power-supplies. In contrast, solid electrolytes conduct only oxygen ions and require such external circuitry to be operative.

Membranes formed from solid electrolytes and mixed conducting oxides are oxygen selective and can transport oxygen ions through dynamically formed oxygen anion vacancies in the solid lattice when such membranes are subjected to temperatures typically above about 500° C. Examples of solid electrolytes include yttria-stabilized zirconia (YSZ) and bismuth oxide. Examples of mixed conductors include titania-doped YSZ, praseodymia-modified YSZ, and, more importantly, various mixed metal oxides some of which possess the perovskite structure.

Membranes formed from mixed conducting oxides which are operated at elevated temperatures can be used to selectively separate oxygen from an oxygen-containing gaseous mixture when a difference in oxygen partial pressures exists on opposite sides of the membrane. Oxygen transport occurs as molecular oxygen is dissociated into oxygen ions which ions migrate to the low pressure side of the membrane where the ions recombine to form oxygen molecules while electrons migrate in a direction opposite the oxygen ions to conserve charge. The rate at which oxygen permeates through the membrane is mainly controlled by two factors, the diffusion rate within the membrane and the kinetic rate of interfacial oxygen exchange; i.e., the rate at which oxygen molecules in the feed gas are converted to mobile oxygen ions at the surface of the feed side of the membrane and back again to oxygen molecules on the permeate side of the membrane.

Membranes formed from mixed conducting oxides offer substantially superior oxygen selectivity than polymeric membranes. However, the value of such improved selectivity must be weighed against the higher costs associated with building and operating plants employing membranes formed from mixed conducting oxides because such plants require heat exchangers, high temperature seals and other costly equipment. Typical prior art membranes formed from mixed conducting oxides do not exhibit sufficient oxygen permeance to justify their use in commercial gas separation applications.

Japanese patent application 61-3-4169 discloses an oxygen permeation apparatus which utilizes a membrane formed from a mixed sintered body consisting of $Sr_{(1+x)/2}La_{(1-x)/2}Co_{1-x}Me_xO_{3-d}$ and $SrMe'O_3$ where Me=Fe, Mn, Cr or Va, $0<=x<=1$ and Me'=Ti, Zr and Hf. The examples state that modest improvements in oxygen anion conductivity can be achieved by impregnating the entire surfaces of such membranes by immersing the sintered membrane bodies into solutions of silver-, palladium- or platinum-containing compounds.

*Solid State Ionics* 37, 253–259 (1990) further describes the membranes presented in Japanese patent application 61-3-4169 wherein palladium metal is added to the mixture of metallic oxides prior to sintering the mixture of metallic oxides to form a palladium-containing multicomponent metallic oxide. Sintered samples containing palladium showed a higher "oxygen anion conductivity" than samples which did not contain palladium.

U.S. Pat. No. 4,791,079 teaches novel mixed ion- and electron-conducting catalytic ceramic membranes consisting of a first layer of impervious mixed ion- and electron-conducting ceramic material and a second layer which is a porous catalyst-containing ion-conducting ceramic material. A preferred composition for the second ion-conducting layer is zirconia stabilized with 8 to 15 mole % calcia, yttria, scandia, magnesia and/or mixtures thereof. The reference neither teaches or suggests forming the porous layer from a mixed conducting ceramic material, namely, a material which conducts both electrons and oxygen ions at elevated temperature. The membranes are suitable for use in hydrocarbon oxidation and dehydrogenation processes.

Researchers are continuing their search for thin, ceramic membranes which exhibit superior oxygen flux and sufficient mechanical strength and properties to enable their use in commercial processes.

BRIEF SUMMARY OF THE INVENTION

The present invention relates to novel composite ion transport membranes having a catalyzed porous layer which are suitable for use in a wide variety of process applications. According to the most general embodiment, the ion transport membranes comprise a porous mixed conducting multicomponent metallic oxide layer having a first surface onto which a catalyst is deposited and a second surface which is contiguous with a dense mixed conducting multicomponent metallic oxide layer having no connected through porosity. Throughout the Specification and Claims, the porous layer onto which a catalyst is deposited shall be referred to as the "catalyzed" porous layer and the "dense" layer shall be interpreted to possess no connected through porosity.

In an alternate embodiment, the ion transport membranes comprise a porous mixed conducting multicomponent metallic oxide layer having a first surface onto which a catalyst is deposited and a second surface which is contiguous with a dense mixed conducting layer, which dense mixed conducting layer is contiguous with an additional porous layer. The porous layer onto which a catalyst has not been deposited is referred to as the "non-catalyzed" porous layer. This embodiment includes ion transport membranes wherein the non-catalyzed porous layer is formed from a mixed conducting multicomponent metallic oxide, an oxygen-ionically conductive material, an electron-conducting material or a material which does not conduct oxygen ions or electrons at membrane operating temperatures in excess of 500° C. Preferably, the non-catalyzed porous layer is fabricated from a mixed conducting multicomponent metallic oxide. The average pore radius of the non-catalyzed porous layer may be constant throughout its cross-section or may increase with distance from the interface with the dense mixed conducting multicomponent metallic oxide layer.

In another alternate embodiment, the ion transport membranes comprise a porous mixed conducting multicomponent metallic oxide layer having a first surface onto which a catalyst is deposited and a second surface which is contiguous with a dense mixed conducting multicomponent metallic oxide layer. The alternate surface of the dense layer is contiguous with a plurality of non-catalyzed porous layers, each respective non-catalyzed porous layer having a discrete average pore radius wherein the average pore radius of each respective non-catalyzed porous layer is larger than the average pore radius of the preceding non-catalyzed porous layer as function of distance from the dense mixed conducting multicomponent metallic oxide layer. Each respective non-catalyzed porous layer may be formed from one or a mixture of multicomponent metallic oxides or a material as previously described. Preferably, the non-catalyzed porous layer adjacent to the dense mixed conducting multicomponent metallic oxide layer is formed from a mixed conducting multicomponent metallic oxide or mixtures thereof.

Applicants have discovered that oxygen flux exhibited by the claimed composite membranes wherein the porous layer onto which the catalyst is deposited is formed from a mixed conducting multicomponent metallic oxide provide unexpectedly superior oxygen flux compared to surface catalyzed membranes presented in U.S. Pat. No. 4,791,079 wherein the porous layer onto which the catalyst is deposited is formed from a ceramic material which conducts oxygen ions but does not conduct electrons at operating temperatures. Stated alternately, U.S. Pat. No. 4,791,079 fails to teach or suggest fabricating a ceramic membrane wherein the porous layer onto which the catalyst is deposited is formed from a mixed conducting material, i.e., a material which conducts both electrons and oxygen ions under operating conditions.

Catalysts used to fabricate the subject ion transport membranes include any material which catalyzes the dissociation of oxygen molecules to oxygen ions or the reassociation of oxygen ions to oxygen molecules. Suitable catalysts include metals and oxides of metals selected from Groups II, V, VI, VII, VIII, IX, X, XI, XV and the F Block lanthanides of the Periodic Table of the Elements according to the International Union of Pure and Applied Chemistry. Suitable metals include platinum, palladium, ruthenium, gold, silver, bismuth, barium, vanadium, molybdenum, cerium, praseodymium, cobalt, rhodium and manganese.

The dense layer and certain specifically enumerated porous layers of the present membranes are formed from one or a mixture of two or more multicomponent metallic oxides, each multicomponent metallic oxide comprising an oxide of at least two different metals or a mixture of at least two different metal oxides wherein the multicomponent metallic oxide demonstrates electron conductivity as well as oxygen ion conductivity at temperatures greater than about 500° C. Hence, these materials are commonly referred to as mixed conducting oxides.

Suitable mixed conducting multicomponent metallic oxides are represented by the structure $A_x A'_{x'} A''_{x''} B_y B'_{y'} B''_{y''} O_{3-z}$, where A,A',A" are chosen from the group comprising Groups 1, 2 and 3 and the F block lanthanides; and B,B',B" are chosen from the D block transition metals according to the Periodic Table of the Elements adopted by the IUPAC wherein $0<x\leq 1$, $0\leq x'\leq 1$, $0\leq x''\leq 1$, $0<y\leq 1$, $0\leq y'\leq 1$, $0\leq y''\leq 1$, $x+x'+x''=1$, $y+y'+y''=1$ and z is a number which renders the compound charge neutral. Preferably, A, A' or A" of the enumerated structure is a Group 2 metal selected from the group consisting of calcium, strontium, barium and magnesium. Preferred mixed conducting oxides are represented by the formula $La_x A_{1-x} Co_y Fe_{1-y} O_{3-z}$ wherein x is between 0 and 1, y is between 0 and 1 and A is selected from barium, strontium or calcium.

The surface catalyzed ion transport membranes of the present invention can be incorporated into any process wherein the gaseous reactants or products formed from the same do not unduly impact membrane performance. Suitable processes include oxygen production, oxidation of organic compounds including hydrocarbons, decomposition of nitrogen- and sulfur-oxides and the like. For example, oxygen can be separated from an oxygen-containing gaseous mixture by introducing an oxygen-containing gaseous mixture into a first gas compartment which is separated from a second gas compartment by one of Applicants' surface catalyzed ion transport membranes and establishing a positive oxygen partial pressure difference between the first and second gas compartments by producing an excess oxygen partial pressure in the first gas compartment and/or by producing a reduced oxygen partial pressure in the second gas compartment. The ion transport membrane is situated such that the oxygen-containing feed gas is contacted with the catalyzed surface of the membrane. The oxygen-containing gaseous mixture is contacted with the membrane at a temperature greater than about 500° C. to separate the oxygen-containing gaseous mixture into an oxygen permeate stream and an oxygen-depleted gaseous stream and recovering the oxygen permeate stream.

DETAILED DESCRIPTION OF THE INVENTION

Figure 1A:
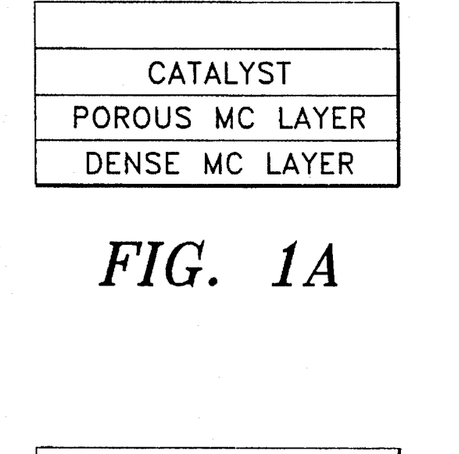
FIG. 1A presents a surface catalyzed ion transport membrane comprising a porous mixed conducting (MC) multicomponent metallic oxide layer having a first surface onto which a catalyst is deposited and a second surface which is contiguous with a dense MC multicomponent metallic oxide layer.

The present invention relates to novel surface catalyzed ion transport membranes which are suitable for use in a wide variety of process applications including processes for separating oxygen from oxygen-containing gaseous mixtures. According to the most general embodiment depicted in FIG. 1A, the surface catalyzed ion transport membranes have a composite structure comprising a porous mixed conducting multicomponent metallic oxide layer having a first surface onto which a catalyst is deposited ("the catalyzed porous layer") and a second surface which is contiguous with a dense mixed conducting multicomponent metallic oxide layer.

The configuration of Applicants' ion transport membranes diverge from the prior art by placing the enumerated catalysts on a porous layer formed from a mixed conducting multicomponent metallic oxide instead of a porous layer formed from an oxygen ionically conductive material which is not electrically conductive. Applicants' ion transport membranes provide unexpectedly improved oxygen flux over the membranes of the prior art such as those described in U.S. Pat. No. 4,791,079 and Japanese patent application 61-3-4169 and the article presented in Solid State Ionics 37, 253–259 (1990), recited under the section entitled, Background of the Invention.

The claimed ion transport membranes comprise a composite structure of a dense layer and a porous layer formed from one or a mixture of two or more mixed conducting multicomponent metallic oxides, each multicomponent metallic oxide comprising an oxide of at least two different metals or a mixture of at least two different metal oxides wherein the multicomponent metallic oxide demonstrates electron conductivity as well as oxygen ion conductivity at temperatures greater than about 500° C. Hence, these materials are commonly referred to as mixed conducting oxides.

Suitable mixed conducting multicomponent metallic oxides are represented by the structure $A_x A'_{x'} A''_{x''} B_y B'_{y'} B''_{y''} O_{3-z}$, where A,A',A" are chosen from the group comprising Groups 1, 2 and 3 and the F block lanthanides; and B,B',B" are chosen from the D block transition metals according to the Periodic Table of the Elements wherein $0<x\leq 1$, $0\leq x'\leq 1$, $0\leq x''\leq 1$, $0<y\leq 1$, $0\leq y'\leq 1$, $0\leq y''\leq 1$, $x+x'+x''=1$, $y+y'+y''=1$ and z is a number which renders the compound charge neutral. All references made to the Periodic Table of the Elements in the Specification and Claims shall refer to the Table adopted by the International Union of Pure and Applied Chemistry.

Preferably, A, A' or A" of the enumerated structure is a Group 2 metal selected from the group consisting of calcium, strontium, barium and magnesium. The dense multicomponent metallic oxide layer typically demonstrates an oxygen ionic conductivity ranging from 0.01 ohm$^{-1}$cm$^{-1}$ to 100 ohm$^{-1}$cm$^{-1}$ and an electronic conductivity ranging from about 1 ohm$^{-1}$cm$^{-1}$ to 100 ohm$^{-1}$cm$^{-1}$.

Preferred mixed conducting multicomponent metallic oxides are represented by the formula $La_x A_{1-x} Co_y Fe_{1-y} O_{3-z}$ wherein x is between 0 and 1, y is between 0 and 1 and A is selected from barium, strontium or calcium. Most preferably, the dense layer is formed from a multicomponent metallic oxide selected from the group consisting of $La_{0.2}Ba_{0.8}Co_{0.8}Fe_{0.2}O_{3-z}$, $Pr_{0.2}Ba_{0.8}Co_{0.8}Fe_{0.2}O_{3-z}$ and $La_{0.2}Ba_{0.8}Co_{0.6}Cu_{0.2}Fe_{0.2}O_{3-z}$.

Catalysts to be deposited onto the enumerated surface of the porous mixed conducting layer of the ion transport membrane include any material which catalyzes the dissociation and ionization of oxygen molecules to oxygen ions. Suitable catalysts include metals and oxides of metals selected from Groups II, V, VI, VII, VIII, IX, X, XI, XV and the F Block lanthanides of the Periodic Table of the Elements. Suitable metals include platinum, palladium, gold, silver, bismuth, barium, vanadium, molybdenum, cerium, praseodymium, cobalt, ruthenium, rhodium and manganese.

The catalyst can be dispersed throughout the porous layer or it may be supported on the surface of the porous layer. If the surface of the porous layer is only partially covered with catalyst, then the catalyst is preferably deposited as close as possible to the interface between the porous and dense mixed conducting multicomponent metallic oxide layers. For example, the desired catalyst can be deposited on the surface of the porous layer by precipitation or adsorption from solution followed by activation at elevated temperature. Alternatively, the catalyst can be incorporated into the porous layer by mixing the catalyst with the powder of the multicomponent metallic oxide prior to sintering the same to form a catalyst-containing porous mixed conducting oxide layer.

The catalyst can be applied in a wide variety of methods. For example, the catalyst can be applied to the porous mixed conducting layer of the ion transport membrane by any conventional method including painting a suspension of metal particles onto the porous layer of the membrane; spraying a solution of metal salt onto the porous layer surface or dispersing a metal salt solution onto the same. Other suitable methods include screen printing, dip coating, plasma spraying and flame spraying, physical vapor deposition such as electron bean evaporation or sputtering, and chemical vapor deposition. The enumerated techniques are well known in the art and can be practiced without undue experimentation. Applicants emphasize that the entire surface of the porous mixed conducting layer does not have to be coated with catalyst in order to achieve the unexpected benefits of the present invention. For example, any selected pattern of catalyst may be deposited onto the surface of the porous mixed conducting layer of the composite membrane by screen printing, masking and other techniques. Such patterns can be designed and applied according to currently used techniques which are well known in the art.

Referring now to the painting technique for applying catalyst to the porous layer of the composite membrane, the following general procedure is utilized. A desired catalyst, such as platinum, may be applied by coating the enumerated porous layer of the composite catalyst. For example, platinum ink #6926 which is commercially available from Engelhard Inc., consisting of micron-sized platinum particles suspended in terpene can be applied to the porous layer of the composite catalyst using a brush or roller. The ink coating is air dried and the membrane is loaded into an apparatus and slowly heated to a temperature above about 500° C. in order to volatilize and burn organic binders and solvents which may be present in the catalyst ink.

Catalysts may also be applied to the surface of the porous mixed conducting layer by spraying the surface with a solution of the desired catalyst. For example, platinum can be applied in this manner using a 0.01 molar solution of platinum acetylacetonate $Pt(Acac)_2$ which was prepared by dissolving an appropriate amount of $Pt(Acac)_2$ in acetone. This solution is loaded into a chromatography sprayer using nitrogen as a carrier gas. The solution is sprayed onto the surface of the porous layer of the composite membrane to yield a 50 nm thick continuous coating of platinum. The acetone solvent is evaporated thereby providing a composite membrane whose porous mixed conducting layer was coated with $Pt(Acac)_2$. The membrane is then loaded into a test apparatus and slowly heated to a temperature greater than about 500° C. The temperature should be sufficiently high to decompose the $Pt(Acac)_2$ to produce the platinum catalyst on the porous mixed conducting layer of the ion transport membrane and organic vapors.

A desired catalyst may also applied to the surface of the porous mixed conducting layer of a composite membrane by depositing a solution of the desired catalyst in an appropriate solvent. For example, a solution of $Pt(Acac)_2$ in acetone can be transferred or dispersed onto the surface of the porous mixed conducting layer of the composite ion transport membrane. The acetone is evaporated leaving the porous mixed conducting layer of the composite membrane coated with $Pt(Acac)_2$. The membrane is heated to decompose the $Pt(Acac)_2$ to form the desired coating of platinum catalyst on the surface of the porous layer of the ion transport membrane.

Figure 1B:
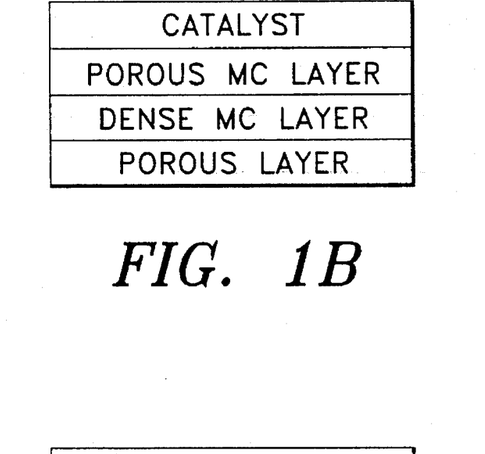
FIG. 1B presents a surface catalyzed ion transport membrane comprising a porous MC multicomponent metallic oxide layer having a first surface onto which a catalyst is deposited and a second surface which is contiguous with a dense MC multicomponent metallic oxide layer which is contiguous with a non-catalyzed porous layer.

In an alternate embodiment depicted in FIG. 1B, the surface catalyzed ion transport membranes comprise a porous mixed conducting (MC) multicomponent metallic oxide layer having a first surface onto which a catalyst is deposited ("the catalyzed porous layer") and a second surface which is contiguous with a dense MC multicomponent metallic oxide layer. The dense layer is situated contiguous with a porous layer onto which a catalyst is not deposited (referred to as the "non-catalyzed porous layer"). This embodiment includes ion transport membranes wherein the non-catalyzed porous layer is formed from a mixed conducting multicomponent metallic oxide, an oxygen-ionically conductive material, an electron-conducting material or a material which does not conduct oxygen ions or electrons at membrane operating temperatures. Preferably, porous layers contiguous with the dense mixed conducting layer are fabricated from one or a mixture of mixed conducting multicomponent metallic oxides described in this Specification.

Figure 1C:
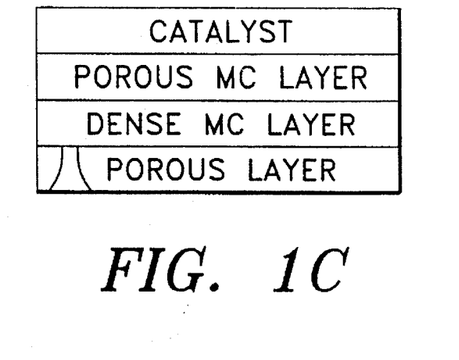
FIG. 1C presents a surface catalyzed ion transport membrane comprising a porous MC multicomponent metallic oxide layer having a first surface onto which a catalyst is deposited and a second surface which is contiguous with a dense MC multicomponent metallic oxide layer which is contiguous with a plurality of individually deposited non-catalyzed porous layers having successively larger pore radii as a function of distance away from the dense MC layer.

In another alternate embodiment, the surface catalyzed ion transport membranes comprise a plurality of non-catalyzed porous layers wherein the average pore radius of each respective non-catalyzed porous layer increases with distance from the interface with the dense mixed conducting multicomponent metallic oxide layer as depicted in FIG. 1C. According to this embodiment, the non-catalyzed porous layer (i.e., the porous layer which does not support the catalyst) may be formed of a porous mixed conducting multicomponent metallic oxide, an oxygen-ionically conductive material, an electron-conducting material or a material which does not conduct electrons or oxygen ions under operating temperatures. Any number of layers are used such that the non-catalyzed porous layer effectively possesses a pore structure which is funnel-shaped with an average pore radius increasing from 0.5 to about 10 micrometers or more moving away from the interface with the dense mixed conducting oxide layer. These layers can be fabricated by starting with a green state formed of a plurality of layers wherein each respective layer comprises successively larger particles. A preferred technique for manufacturing ultrathin solid state membranes is presented in United Stated patent application Ser. No. 07/816,206, filed on Jan. 3, 1992, now U.S. Pat. No. 5,160,618, patented Nov. 3, 1992, which is assigned to Air Products and Chemicals, Inc., Allentown, Pa.

Figure 1D:
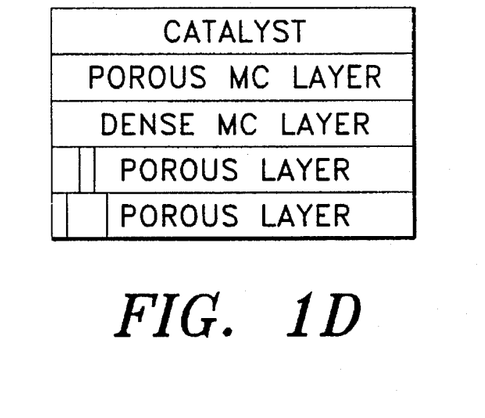
FIG. 1D presents a surface catalyzed ion transport membrane comprising a porous MC layer having a first surface onto which a catalyst is deposited and a second surface which is contiguous with a dense MC layer which is contiguous with two or more discrete non-catalyzed porous layers wherein each respective porous layer has a successively larger average pore radius as a function of distance away from the dense MC layer.

In another alternate embodiment depicted in FIG. 1D, the ion transport membranes comprise a porous mixed conducting multicomponent metallic oxide layer having a first surface onto which a catalyst is deposited ("the catalyzed porous layer") and a second surface which is contiguous with a dense mixed conducting multicomponent metallic oxide. Further, a plurality of non-catalyzed porous layers having successively larger average pore radii as a function of distance away from the dense mixed conducting oxide layer are formed contiguous to the side of the dense mixed conducting oxide layer opposite the catalyzed porous layer.

Each respective non-catalyzed porous layer of the membranes of the embodiment according to FIG. 1D may be formed from one or a mixture of multicomponent metallic oxides, an oxygen-ionically conductive material, an electron-conducting material or a material which does not conduct electrons or oxygen ions under operating temperatures. Preferably, the non-catalyzed porous layer adjacent to the dense mixed conducting multicomponent metallic oxide layer is formed from a multicomponent metallic oxide or mixtures thereof and preferably has an average pore radius of less than about 10 micrometers while the average pore radius of each subsequent non-catalyzed porous layer has an average pore radius which progressively increases as a function of distance from the dense layer. Any combination of non-catalyzed porous layers can be utilized so long as their coefficients of thermal expansion are compatible and chemical reactions are minimized between the respective layers at membrane operating temperatures.

Examples of suitable porous materials which are not mixed conducting under process operating conditions include high temperature oxygen compatible metal alloys, metal oxide-stabilized zirconia such a yttria-stabilized zirconia and calcium-stabilized zirconia, ceria, alumina, magnesia, silica, titania and compounds and mixtures thereof.

Figure 1E:
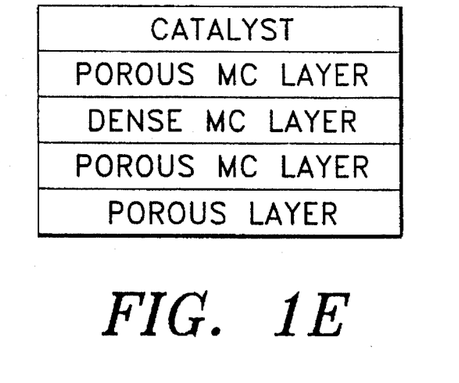
FIG. 1E presents a surface catalyzed ion transport membrane comprising a porous MC layer having a first surface onto which a catalyst is deposited and a second surface which is contiguous with a dense MC layer which is contiguous with a plurality of non-catalyzed porous layers wherein one or more of the non-catalyzed porous layers not in contact with the dense mixed conducting oxide layer is formed of a material which is not a mixed conductor.

FIG. 1E illustrates a surface catalyzed ion transport membrane similar to the embodiment described in FIG. 1D except that the non-catalyzed porous layer which is contiguous with the dense mixed conducting multicomponent metallic oxide layer is necessarily formed from a mixed conducting multicomponent metallic oxide. Any combination of multicomponent metallic oxides can be used so long as the dense and porous layers are chemically and mechanically compatible under conditions used in the enumerated applications such as in a process for separating oxygen from an oxygen-containing gaseous mixture.

The thickness of the porous layers of the composite membranes referred to in each of the above-mentioned embodiments can be varied to ensure sufficient mechanical strength of the composite membrane. The desired thickness of each porous layer is regulated by the following considerations. First, the porosity and average pore radius of each porous layer should be regulated such that oxygen flux is not impeded while maintaining sufficient mechanical strength. Second, the pores or channels of pores within each porous layer should be wide enough so that oxygen flux is not impeded, but not so wide as to cause pore filling during fabrication or fissure of the dense layer during operation. Third, each porous layer should be compatible with the dense layer in terms of chemical reactivity and adhesion and thermal expansion to reduce problems associated with cracking and delamination.

In the case where the porous layers of the composite membrane are formed from mixed conducting multicomponent metallic oxides, such porous layers act as a compatible mechanical support for the dense mixed conducting oxide layer and provide two interacting diffusion paths for oxygen; through the pores, and through the solid. Surface kinetic rate limitations for gas-solid oxygen exchange are mitigated by the availability of a large "active" surface area in the small pore structure of the support, especially in the vicinity of the dense mixed conducting oxide layer. On the other hand, the effect of the small pores in hindering diffusion is mitigated by fast ionic conduction in the solid.

The thickness of the dense mixed conducting layer typically ranges from 0.01 micrometer to about 500 micrometers although preferably, the dense layer is fabricated as thinly as permitted by structural integrity considerations and has a thickness of less than about 100 micrometers. The porous mixed conducting oxide layer contiguous with the dense mixed conducting layer typically has a thickness ranging from 1 micrometer to about 2 millimeters. Porous layers not in contact with the dense mixed conducting layer, whether formed from a mixed conducting oxide or a material which is not a mixed conducting oxide, can be as thick as desired to ensure mechanical strength to the extent that the ultimate thickness does not impede gas diffusion. Typically, the total thickness of the composite membrane is less than about 5 mm, although membranes having a greater thickness are also contemplated.

Surface catalyzed ion transport membranes of this invention which utilize one or more active porous supports formed from mixed conducting oxides provide particularly high oxygen flux because such active porous layers counteract surface kinetic limitations by increasing the active gas-solid interfacial area per unit volume. Therefore, as the average pore radius is reduced while maintaining a given porosity within each porous layer, surface kinetic limitations which reduce oxygen flux can be correspondingly diminished. A fairly thin porous mixed conducting oxide layer having an average pore radius ranging from 0.1 to about 10 micrometers, situated contiguous with a dense mixed conducting layer provides increased interfacial area to counteract surface kinetic limitations, but does not cause any significant pressure drop or resistance to mass transfer.

Thin dense layers of a desired mixed conducting multicomponent metallic oxide can be deposited in a variety of thicknesses onto the enumerated non-mixed conducting or mixed conducting multicomponent metallic oxide porous layers by known techniques. For example, the membrane composites can be manufactured by first forming a porous body from relatively coarse sized particles of the desired material. A slurry of finer particles of a compatible multicomponent metallic oxide may then be coated onto the porous body and cured to the green state, the two layer system then being fired to form the composite membrane.

Alternatively, the composite membranes of the present invention can be prepared by applying a dense layer of a desired mixed conducting oxide onto the desired porous substrate by conventional chemical vapor deposition techniques followed by sintering to obtain the desired dense layer. In order to obtain an optimal dense coating, a smaller average pore radius in the surface of the porous support may be used compared to the average pore radius in the bulk. This may be achieved by using two or more porous layers which differ in properties such as pore radius and porosity.

The catalyzed porous mixed conducting layer may then be applied to the second surface of the thin dense layer by a variety of techniques, for example, dip coating with a slurry or suspension of powder or spraying a suspension of powder, followed by drying and firing. The catalyst may then be applied to this layer as previously described.

The advantages afforded by Applicants' surface catalyzed ion transport membranes can best be understood by developing a thorough understanding of the mechanism by which oxygen is ionically transported through the dense mixed conducting oxide layer of an ion transport membrane. The oxygen flux observed by a conventional ion transport membrane is controlled by "surface kinetic limitations" and "bulk diffusion limitations". Surface kinetic limitations are constraints to oxygen flux caused by one or more of the many steps involved in converting an oxygen molecule in the gas phase on the feed side of the ion transport membrane into mobile oxygen ions and converting the oxygen ions back to oxygen molecules on the permeate side of the ion transport membrane. Bulk diffusion limitations are constraints on oxygen flux relating to the diffusivity of oxygen ions through the dense mixed conducting oxide layer. Additional diffusion constraints can be associated with molecular oxygen moving through the pores of the porous layers.

The present invention provides surface catalyzed composite membranes which overcome kinetic limitations on oxygen flux associated with very thin dense mixed conducting oxide layers while providing membranes which maintain their structural integrity under the demanding high temperature conditions associated with processes using such membranes.

The membranes of the present invention can be used to recover oxygen from an oxygen-containing gaseous mixture by delivering the oxygen-containing gaseous mixture into a first gas compartment which is separated from a second gas compartment by the subject membrane, establishing a positive oxygen partial pressure difference between the first and second gas compartments by producing an excess oxygen partial pressure in the first gas compartment and/or by producing a reduced oxygen partial pressure in the second gas compartment; contacting the oxygen-containing gaseous mixture with the catalyzed surface of the enumerated ion transport membranes at a temperature greater than about 500° C. to separate the compressed oxygen-containing gaseous mixture into an oxygen permeate stream and an oxygen-depleted gaseous stream and recovering the oxygen permeate stream.

Any conventional apparatus can be utilized to house the ion transport membranes of the present invention whereby the membrane forms a partition between the first and second gas compartments. A representative apparatus is disclosed in U.S. Pat. No. 5,035,727, issued to Air Products and Chemicals, Inc., Allentown, Pa. The surface catalyzed ion transport membranes are situated in the apparatus such that the oxygen-containing gaseous mixture is contacted with the side of the membrane upon which the catalyst resides.

The composite membranes of this invention are capable of separating oxygen from oxygen-containing gaseous mixtures containing one or more components selected from carbon dioxide, water and volatile hydrocarbons. The amount of oxygen present in such gaseous mixtures typically ranges between about 0.01 vol. % to 50 vol. % oxygen. The preferred oxygen-containing gaseous mixture is atmospheric air.

A difference in oxygen partial pressure between the first and second compartments provides the driving force for effecting the separation when the process temperature is elevated to a sufficient temperature to cause oxygen in the oxygen-containing gaseous mixture residing in the first compartment to adsorb, dissociate and ionize. Oxygen is transported through the membrane in the ionic form. A pure oxygen product is collected in the second gas compartment wherein oxygen ions are converted into neutral oxygen molecules by the release of electrons and reassociation. The second gas compartment resides at lower oxygen partial pressure than the first gas compartment.

A positive oxygen partial pressure difference between the first and second gas compartments can be created by compressing air in the first compartment to a pressure sufficient to recover the oxygen permeate stream at a pressure of greater than or equal to about one atmosphere. Typical pressures range from about 15 psia to about 250 psia and the optimum pressure will vary depending upon the amount of oxygen in the oxygen-containing gaseous mixture. Conventional compressors can be utilized to achieve the compression required to practice the present step of the process. Alternately, a positive oxygen partial pressure difference between the first and second gas compartments can be achieved by evacuating the second gas compartment to a pressure sufficient to recover the oxygen permeate.

The final step of the process comprises recovering the oxygen-containing gaseous mixture by storing the substantially pure oxygen in a suitable container or transferring the same to another process. The oxygen permeate typically comprises pure oxygen or high purity oxygen defined as a gas generally containing at least about 90 vol. % $O_2$, preferably more than about 95 vol % $O_2$ and especially more than 99 vol. % $O_2$.

The surface catalyzed ion transport membranes of the present invention can be incorporated into any process wherein the gaseous reactants or products formed from the same do not unduly impact membrane performance. Suitable processes include oxygen production, oxidation of organic compounds including hydrocarbons, decomposition of nitrogen- and sulfur-oxides and the like.

The following examples are provided to further illustrate Applicants' claimed process. Such examples are illustrative and are not intended to limit the scope of the appended claims.

EXAMPLE 1

(Theoretical) Process for Recovering Oxygen from an Oxygen-containing Gaseous Mixture Using a Surface Catalyzed Composite Ion Transport Membrane The mathematical model found in U.S. Pat. No. 5,240,480 (the '480 patent) can be used to describe oxygen transport through a surface catalyzed ion transport membrane comprising a dense mixed conducting multicomponent metallic oxide layer having a porous layer on either or both sides of the dense layer. Table 2 of the '480 patent lists the parameters of the non-catalyzed dense mixed conducting multicomponent metallic oxide layer. Table 1 provided below lists the parameters of the catalyzed porous layer of an ion transport membrane according to FIG. 1A which consists of a porous mixed conducting oxide layer having a first surface onto which a metallic catalyst has been deposited and a second surface which is contiguous with a dense mixed conducting multicomponent metallic oxide layer. Parameters $k_1$, $k_2$, $k_a$ and $k_d$ were obtained by applying a least square fitting of data resulting from the enhanced surface kinetics obtained upon applying platinum to the surface of the $La_{0.2}Ba_{0.8}Co_{0.8}Fe_{0.2}O_{3-z}$ layer.

TABLE 1

MODEL PARAMETERS OF A
SURFACE CATALYZED COMPOSITE MEMBRANE
COMPOSITION: $La_{0.2}Ba_{0.8}Co_{0.8}Fe_{0.2}O_{3-z}$
TEMPERATURE: 850° C.

| Parameter | Value |
| --- | --- |
| $A_{A'}$ | 0.0207 atoms/cm$^3$ |
| $N_o$ | 0.0777 atoms/cm$^3$ |
| m | 1.04e-9 atoms/cm$^3$ |
| $D_p$ | 2e-2 cm$^2$/sec |
| $D_i$ | 4e-5 cm$^2$/sec |
| $k_1$ | 4.4e-5 1/sec |
| $k_2$ | 13.3 cm$^7$/atoms$^2$/sec |
| $k_a$ | 9.2e-2 moles/cm$^2$/sec/atm |
| $k_d$ | 1.15e-2 atoms/cm$^2$/sec |

Feed side mixed conducting porous layer—$La_{0.2}Ba_{0.8}Co_{0.8}Fe_{0.2}O_{3-z}$ coated with 10 mg platinum catalyst/cm$^2$ surface, 1 μm thick, 0.1 μm radius pores, 32% porosity Dense Layer—$La_{0.2}Ba_{0.8}Co_{0.8}Fe_{0.2}O_{3-z}$ 20 μm thickness P($O_2$) membrane dense layer side=0.001 atm P($O_2$) membrane porous catalyzed layer side=0.21 atm Temp.=850° C.

The results obtained using the computer simulation are as follows: Run 1, which utilized a membrane wherein a catalyst was applied to a porous layer which conducts only oxygen-ions in the manner of U.S. Pat. No. 4,791,079, provided an oxygen flux of 3.81 sccm/cm$^2$. Run 2, which utilized a membrane according to the present invention wherein a metallic catalyst was applied to a porous mixed conducting multicomponent metallic oxide layer of the ion transport membrane provided an oxygen flux of 9.97 sccm/cm$^2$. A comparison of the results obtained under Runs 1 and 2 demonstrate that a 78% increase in oxygen flux is obtained when a catalyst is applied to a porous layer formed from a mixed conducting multicomponent metallic oxide versus a porous layer formed merely from an oxygen-ionically conductive material.

EXAMPLE 2

(Theoretical) Process for Recovering Oxygen from an Oxygen-Containing Gaseous Mixture Using a Surface Catalyzed Composite Ion Transport Membrane The mathematical model found in U.S. Pat. No. 5,240,480 (the '480 patent) was utilized to describe oxygen transport through a surface catalyzed ion transport membrane comprising a dense mixed conducting multicomponent metallic oxide layer having a porous layer on both sides of the dense layer. Table 2 of the '480 patent lists the parameters of the non-catalyzed mixed conducting multicomponent metallic oxide layer. Table 2 provided below lists the parameters of a catalyzed mixed conducting layer of an ion transport membrane according to FIG. 1E which consists of a dense mixed conducting multicomponent metallic oxide layer having a first surface which is contiguous with a mixed conducting multicomponent metallic oxide porous layer onto which a catalyst has been deposited and a second surface which is contiguous to another mixed conducting porous layer. Additionally, the mixed conducting porous layer on the second surface of the dense mixed conducting oxide layer is supported by an additional porous layer which is not mixed conducting under process operating conditions. The parameters used in the computer simulation are summarized in Table 2.

TABLE 2

MODEL PARAMETERS OF A
SURFACE CATALYZED COMPOSITE MEMBRANE
COMPOSITION: $La_{0.2}Ba_{0.8}Co_{0.8}Fe_{0.2}O_{3-x}$
TEMPERATURE: 850° C.

| Parameter | Value |
|---|---|
| $A_{A'}$ | 0.0207 atoms/cm$^3$ |
| $N_o$ | 0.0777 atoms/cm$^3$ |
| m | 1.04e-9 atoms/cm$^3$ |
| $D_p$ | 2e-2 cm$^2$/sec |
| $D_i$ | 4e-5 cm$^2$/sec |
| $k_1$ | 4.4e-5 1/sec |
| $k_2$ | 13.3 cm$^7$/atoms$^2$/sec |
| $k_a$ | 9.2e-2 moles/cm$^2$/sec/atm |
| $k_d$ | 1.15e-2 atoms/cm$^2$/sec |

Feed side mixed conducting porous layer—$La_{0.2}Ba_{0.8}Co_{0.8}Fe_{0.2}O_{3-z}$ coated with 10 mg platinum catalyst/cm$^2$ surface, 1 μm thick, 0.1 μm radius pores, 32% porosity Dense Layer—$La_{0.2}Ba_{0.8}Co_{0.8}Fe_{0.2}O_{3-z}$ 5 μm thickness Permeate side mixed conducting porous layer—$La_{0.2}Ba_{0.8}Co_{0.8}Fe_{0.2}O_{3-z}$ 1 μm thick, 0.1 μm radius pores, 32% porosity Porous support layer—32% porosity, 5 μm diameter pores 1.495 mm thick $P(O_2)$ membrane catalyzed porous feed side layer=0.21 atm $P(O_2)$ membrane non-catalyzed porous layer side=0.001 atm Temp.=850° C.

The results obtained using the computer simulation are as follows: Run 3, which utilized a membrane wherein a metal catalyst was not applied to the feed-side porous mixed conducting oxide layer, wherein the parameters recited in Table 2 of the '480 Patent were utilized, provided an oxygen flux of 15.28 sccm/cm$^2$. Run 4, which utilized a membrane wherein a metal catalyst was applied to the feed side porous mixed conducting oxide layer of the ion transport membrane, as illustrated in Table 2 above, provided an oxygen flux of 18.82 sccm/cm$^2$. A comparison of the results obtained under Runs 3 and 4 demonstrate that a 19% increase in oxygen flux is obtained when a catalyst is applied to the feed side porous mixed conducting oxide layer of the composite membrane.

Applicants have demonstrated that unexpectedly superior oxygen flux is obtained when the enumerated catalysts are deposited onto the porous mixed conducting layer of the composite membrane which is contiguous to a dense mixed conducting multicomponent metallic oxide layer. Since the surface catalyzed ion transport membranes of the present invention exhibit increased oxygen flux compared to corresponding prior art membranes, commercial plants which utilize Applicants' surface catalyzed ion transport membranes require a smaller surface area to achieve a given oxygen production rate than prior art membranes.

Having described their present invention, Applicants inventive contribution is described in the following claims.

We claim:

1. An ion transport membrane comprising a porous mixed conducting multicomponent metallic oxide layer having a first surface which is coated with a catalyst and a second surface which is contiguous with a dense mixed conducting multicomponent metallic oxide layer.

2. The ion transport membrane according to claim 1 wherein the catalyst is a metal or an oxide of a metal selected from Groups X and XI of the Periodic Table of the Elements.

3. The ion transport membrane according to claim 2 wherein the metal is selected from the group consisting of platinum, palladium, gold and silver.

4. The ion transport membrane according to claim 1 wherein the catalyst is a metal or an oxide of a metal selected from Groups II, V, VI, VII, VIII, IX, XV and the F Block lanthanides.

5. The ion transport membrane according to claim 4 wherein the metal is selected from the group consisting of bismuth, barium, vanadium, molybdenum, cerium, ruthenium, manganese, cobalt, rhodium and praseodymium.

6. The ion transport membrane according to claim 1 wherein the dense multicomponent metallic oxide layer and the porous multicomponent metallic oxide layer are independently formed from one or a mixture of multicomponent metallic oxides represented by the formula $A_xA'_{x'}A''_{x''}B_yB'_{y'}B''_{y''}O_{3-z}$, where A,A',A'' are chosen from the group comprising Groups 1, 2 and 3 and the F block lanthanides; and B,B',B'' are chosen from the D block transition metals according to the Periodic Table of the Elements wherein $0<x\leq1$, $0\leq x'\leq1$, $0\leq x''23\ 1$, $0<y\leq1$, $0\leq y'\leq1$, $0\leq y''\leq1$, $x+x'+x''=1$, $y+y'+y''=1$ and z is a number which renders the compound charge neutral.

7. The ion transport membrane according to claim 6 wherein A, A' or A'' of the enumerated formula is a Group 2 metal selected from the group consisting of calcium, strontium, barium and magnesium.

8. The ion transport membrane according to claim 6 wherein the dense layer is formed from a multicomponent metallic oxide represented by the formula $La_xA_{1-x}Co_yFe_{1-y}O_{3-z}$ wherein x is between 0 and 1, y is between 0 and 1 and A is selected from barium, strontium or calcium.

9. The ion transport membrane according to claim 6 wherein the dense layer is formed from a multicomponent metallic oxide is selected from the group consisting of $La_{0.2}Ba_{0.8}Co_{0.8}Fe_{0.2}O_{3-z}$, $Pr_{0.2}Ba_{0.8}Co_{0.8}Fe_{0.2}O_{3-z}$ and $La_{0.2}Ba_{0.8}Co_{0.6}Cu_{0.2}Fe_{0.2}O_{3-z}$ and the metal of the catalyst is platinum.

10. The ion transport membrane according to claim 9 wherein the dense layer has a thickness ranging from 0.01 micrometer to about 500 micrometers and the porous layer has a thickness ranging from 1 micrometer to about 2 millimeters.

11. A process for recovering oxygen from an oxygen-containing gaseous mixture which utilizes the ion transport membrane according to claim 1.

12. A process for oxidizing an organic compound which utilizes the ion transport membrane according to claim 1.

13. A process for converting nitrogen oxides into gaseous nitrogen and oxygen which utilizes the ion transport membrane according to claim 1.

14. A process for converting sulfur oxides into sulfur and oxygen which utilizes the ion transport membrane according to claim 1.

15. A process for converting methane into higher hydrocarbons which utilizes the ion transport membrane according to claim 1.

16. An ion transport membrane comprising a mixed conducting multicomponent metallic oxide porous layer having a first surface and a second surface wherein the first surface is coated with a metallic catalyst and the second surface is contiguous with a first surface of a dense mixed conducting multicomponent metallic oxide layer and a non-catalyzed porous layer which is contiguous with a second surface of the dense mixed conducting multicomponent metallic oxide layer.

17. The ion transport membrane according to claim 16 wherein the non-catalyzed porous layer is formed from a mixed conducting multicomponent metallic oxide, an electronically conductive material, an oxygen-ionically conductive material or a material which does not conduct oxygen ions or electrons at temperatures in excess of 500° C.

18. The ion transport membrane according to claim 16 wherein the catalyst is a metal or an oxide of a metal selected from Groups X and XI of the Periodic Table of the Elements.

19. The ion transport membrane according to claim 18 wherein the metal is selected from the group consisting of platinum, palladium, gold and silver.

20. The ion transport membrane according to claim 16 wherein the catalyst is a metal or an oxide of a metal selected from Groups II, V, VI, VII, VIII, IX, XV and the F Block lanthanides.

21. The ion transport membrane according to claim 20 wherein the metal is selected from the group consisting of bismuth, barium, vanadium, molybdenum, cerium, ruthenium, manganese, cobalt, rhodium and praseodymium.

22. The ion transport membrane according to claim 16 wherein the average pore radius of the non-catalyzed porous layer is less than about 10 micrometers.

23. The ion transport membrane according to claim 16 wherein the dense mixed conducting multicomponent metallic oxide layer and the porous mixed conducting multicomponent metallic oxide layer onto which the catalyst has been deposited are independently formed from one or a mixture of multicomponent metallic oxides represented by the formula $A_xA'_{x'}A''_{x''}B_yB'_{y'}B''_{y''}O_{3-z}$, where A,A',A" are chosen from the group comprising Groups 1, 2 and 3 and the F block lanthanides; and B,B',B" are chosen from the D block transition metals according to the Periodic Table of the Elements wherein $0<x\leq1$, $0\leq x'\leq1$, $0\leq x''23\ 1$, $0<y\leq1$, $0\leq y'\leq1$, $0\leq y''\leq1$, $x+x'+x''=1$, $y+y'+y''=1$ and z is a number which renders the compound charge neutral.

24. The ion transport membrane according to claim 23 wherein A, A' or A" of the enumerated formula is a Group 2 metal selected from the group consisting of calcium, strontium, barium and magnesium.

25. The ion transport membrane according to claim 23 wherein the dense layer is formed from a multicomponent metallic oxide represented by the formula $La_xA_{1-x}Co_yFe_{1-y}O_{3-z}$ wherein x is between 0 and 1, y is between 0 and 1 and A is selected from barium, strontium or calcium.

26. The ion transport membrane according to claim 23 wherein the dense layer is formed from a multicomponent metallic oxide selected from the group consisting of $La_{0.2}Ba_{0.8}Co_{0.8}Fe_{0.2}O_{3-z}$, $Pr_{0.2}Ba_{0.8}Co_{0.8}Fe_{0.2}O_{3-z}$ and $La_{0.2}Ba_{0.8}Co_{0.6}Cu_{0.2}Fe_{0.2}O_{3-z}$.

27. The ion transport membrane according to claim 17 wherein the non-catalyzed porous layer is formed from a material selected from the group consisting of a high temperature oxygen compatible metal alloy, metal oxide-stabilized zirconia such a yttria-stabilized zirconia and calcium-stabilized zirconia, ceria or materials which do not conduct electrons or oxygen ions, such as alumina, magnesia, silica, titania and compounds and mixtures thereof.

28. An ion transport membrane comprising a mixed conducting multicomponent metallic oxide porous layer having a first surface and a second surface wherein the first surface is coated with a metallic catalyst and the second surface is contiguous with a first surface of a dense mixed conducting multicomponent metallic oxide layer and a plurality of non-catalyzed porous layers which are contiguous with a second surface of the dense mixed conducting multicomponent metallic oxide layer.

29. The ion transport membrane according to claim 28 wherein the plurality of non-catalyzed porous layers are formed from a mixed conducting multicomponent metallic oxide, an electrically conductive material, an oxygen-ionically conductive material or a material which does not conduct oxygen ions or electrons at temperatures in excess of 550° C.

30. The ion transport membrane according to claim 29 wherein each respective non-catalyzed porous layer of the plurality of non-catalyzed porous layers has a discrete average pore radius wherein the average pore radius of each respective porous layer is larger than the average pore radius of the preceding porous layer as function of distance from the dense layer.

31. The ion transport membrane according to claim 29 wherein the catalyst is a metal or an oxide of a metal selected from Groups X and XI of the Periodic Table of the Elements.

32. The ion transport membrane according to claim 31 wherein the metal is selected from the group consisting of platinum, palladium, gold and silver.

33. The ion transport membrane according to claim 29 wherein the catalyst is a metal or an oxide of a metal selected from Groups II, V, VI, VII, VIII, IX, XV and the F Block lanthanides.

34. The ion transport membrane according to claim 33 wherein the metal is selected from the group consisting of bismuth, barium, vanadium, molybdenum, cerium, ruthenium, manganese, cobalt, rhodium and praseodymium.

35. The ion transport membrane according to claim 28 wherein the dense mixed conducting multicomponent metallic oxide layer and the porous mixed conducting multicomponent metallic oxide layer onto which the catalyzed has been deposited are independently formed from one or a mixture of multicomponent metallic oxides represented by the formula $A_xA'_{x'}A''_{x''}B_yB'_{y'}B''_{y''}O_{3-z}$, where A,A',A" are chosen from the group comprising Groups 1, 2 and 3 and the F block lanthanides; and B,B',B" are chosen from the D block transition metals according to the Periodic Table of the Elements wherein $0<x\leq1$, $0\leq x'\leq1$, $0\leq x''23\ 1$, $0<y\leq1$, $0\leq y'\leq1$, $0\leq y''\leq1$, $x+x'+x''=1$, $y+y'+y''=1$ and z is a number which renders the compound charge neutral.

36. The ion transport membrane according to claim 35 wherein A, A' or A" of the enumerated formula is a Group 2 metal selected from the group consisting of calcium, strontium, barium and magnesium.

37. The on transport membrane according to claim 35 wherein the dense layer is formed from a multicomponent metallic oxide represented by the formula $La_xA_{1-x}Co_yFe_{1-y}O_{3-z}$ wherein x is between 0 and 1, y is between 0 and 1 and A is selected from barium, strontium or calcium.

38. The ion transport membrane according to claim 35 wherein the dense layer is formed from a multicomponent metallic oxide selected from the group consisting of $La_{0.2}Ba_{0.8}Co_{0.8}Fe_{0.2}O_{3-z}$, $Pr_{0.2}Ba_{0.8}Co_{0.8}Fe_{0.2}O_{3-z}$ and $La_{0.2}Ba_{0.8}Co_{0.6}Cu_{0.2}Fe_{0.2}O_{3-z}$.

39. The ion transport membrane according to claim 38 wherein a non-catalyzed porous layer of the plurality of non-catalyzed porous layers situated contiguous with the dense mixed conducting multicomponent metallic oxide layer is formed from a mixed conducting multicomponent metallic oxide.

40. The ion transport membrane according to claim 39 wherein one or more non-catalyzed porous layers not in contact with the dense mixed conducting multicomponent metallic oxide layer are formed from a material selected from the group consisting of a high temperature oxygen compatible metal alloy, metal oxide-stabilized zirconia such a yttria-stabilized zirconia and calcium-stabilized zirconia, ceria or materials which do not conduct electrons or oxygen ions, such as alumina, magnesia, silica, titania and compounds and mixtures thereof.

* * * * *

UNITED STATES PATENT AND TRADEMARK OFFICE
CERTIFICATE OF CORRECTION

PATENT NO. : 5,534,471

DATED : July 9, 1996

INVENTOR(S) : Michael F. Carolan, et al.

It is certified that error appears in the above-identified patent and that said Letters Patent is hereby corrected as shown below:

Column 14, Line 30
   Delete "23" and substitute therefor -- $\leq 1$ --

Column 15, Line 42
   Delete "23" and substitute therefor -- $\leq 1$ --

Column 16, Line 47
   Delete "23" and substitute therefor -- $\leq 1$ --

Signed and Sealed this

Seventeenth Day of September, 1996

Attest:

BRUCE LEHMAN

*Attesting Officer*        *Commissioner of Patents and Trademarks*